(12) United States Patent
Yabusaki

(10) Patent No.: US 6,667,177 B1
(45) Date of Patent: Dec. 23, 2003

(54) METHOD FOR COUNTING LEUKOCYTES AND APPARATUS FOR COUNTING LEUKOCYTES

(75) Inventor: Katsumi Yabusaki, Tsukuba (JP)

(73) Assignee: Kowa Company, Ltd., Aichi (JP)

( * ) Notice: Subject to any disclaimer, the term of this patent is extended or adjusted under 35 U.S.C. 154(b) by 0 days.

(21) Appl. No.: 09/554,056
(22) PCT Filed: Nov. 10, 1998
(86) PCT No.: PCT/JP98/05043
§ 371 (c)(1),
(2), (4) Date: May 8, 2000
(87) PCT Pub. No.: WO99/24831
PCT Pub. Date: May 20, 1999

(30) Foreign Application Priority Data

Nov. 11, 1997 (JP) ............................................. 9-309069
Dec. 16, 1997 (JP) ............................................. 9-346842

(51) Int. Cl.⁷ ........................ G01N 31/00; G01N 33/48
(52) U.S. Cl. ........................... 436/10; 436/17; 436/63; 436/164; 436/165; 422/73; 422/82.05; 422/72; 382/133; 382/134
(58) Field of Search ........................... 436/10, 17, 63, 436/164, 165; 422/73, 72, 82.05, 82.08, 82.09, 102; 382/128, 133, 134

(56) References Cited

U.S. PATENT DOCUMENTS

| | | | | |
|---|---|---|---|---|
| 4,255,256 A | * | 3/1981 | Ferrante et al. | 210/730 |
| 4,600,507 A | * | 7/1986 | Shimizu et al. | 210/321.84 |
| 4,755,356 A | * | 7/1988 | Robbins et al. | 215/306 |
| 5,225,165 A | * | 7/1993 | Perlman | 206/815 |
| 5,232,857 A | * | 8/1993 | Lefevre et al. | 436/10 |
| 5,254,314 A | * | 10/1993 | Yu et al. | 215/237 |
| 5,334,538 A | * | 8/1994 | Parker et al. | 436/525 |
| 5,389,549 A | * | 2/1995 | Hamaguchi et al. | 435/2 |
| 5,441,894 A | * | 8/1995 | Coleman et al. | 436/518 |
| 5,496,734 A | * | 3/1996 | Sakata | 435/2 |
| 5,552,325 A | * | 9/1996 | Nochumson et al. | 210/657 |
| 5,618,733 A | * | 4/1997 | Sakata et al. | 424/533 |
| 5,900,377 A | * | 5/1999 | Gotti et al. | 210/787 |
| 5,916,521 A | * | 6/1999 | Bunce et al. | 422/56 |
| 6,048,464 A | * | 4/2000 | Tanaka et al. | 210/488 |
| 6,211,953 B1 | * | 4/2001 | Niino et al. | 356/246 |
| 6,252,235 B1 | * | 6/2001 | Niino et al. | 250/458.1 |

FOREIGN PATENT DOCUMENTS

| | | | |
|---|---|---|---|
| EP | 926483 | * | 6/1999 |
| JP | 62-102151 | * | 6/1987 |
| JP | 8-129012 | * | 5/1996 |
| WO | 97/02482 | * | 1/1997 |
| WO | 97/23266 | * | 7/1997 |

* cited by examiner

Primary Examiner—Maureen M. Wallenhorst
(74) Attorney, Agent, or Firm—Kilpatrick Stockton LLP

(57) ABSTRACT

A leukocyte accumulation container having an opening, a sidewall portion and a bottom portion, part or all of the sidewall portion having a horizontal section area gradually increasing in a direction from the bottom portion towards the opening. A cytolytic agent is added to a solution of a platelet preparation or a solution of an erythrocyte preparation to solubilize platelets or erythrocytes in the solution of the preparation. The leukocyte accumulation container then is set on a centrifuge to accumulate the leukocytes on the bottom portion of the leukocyte accumulation container, and the leukocytes accumulated on the bottom portion are counted.

15 Claims, 8 Drawing Sheets

METHOD FOR COUNTING LEUKOCYTES AND APPARATUS FOR COUNTING LEUKOCYTES

TECHNICAL FIELD

The present invention relates to a method for counting leukocytes and an apparatus for counting leukocytes. In particular, the present invention relates to a method and an apparatus suitable to count leukocytes in a platelet preparation or an erythrocyte preparation.

BACKGROUND ART

Platelet preparations and erythrocyte preparations are mainly used for alleviation of thrombocytopenia and anemia, surgical operations and so forth. Considering side effects and the like, it is not desirable from a viewpoint of quality that leukocytes are present in a platelet preparation or an erythrocyte preparation. Thus, the number of leukocytes that can be contained in a small amount in a platelet preparation or an erythrocyte preparation is measured for quality control.

Usually, the leukocyte count in a platelet preparation or an erythrocyte preparation is measured by baring nuclei of leukocytes and staining them. That is, leukocytes are accumulated by a centrifuge or the like, stained and then placed in a Nageotte chamber (hemocytometer) so that observers visually count the number using a microscope. Since platelets are rarely dissolved in this method, however, leukocytes are buried in the platelets, which results in deteriorated measurement accuracy. In addition, visual measurement is extremely inefficient. Furthermore, in this measurement method, observers often contact blood preparations with a possibility of biohazard (biological contamination). Therefore, a safe method that achieves automatization and facilitation of the measuring operation as well as improvement of measurement accuracy is presently desired.

On the other hand, in general, nuclei of leukocytes must be bared to stain the leukocytes for measurement. It has been known that a surfactant is added for this purpose. However, no method for counting leukocytes has been known, wherein a cytolytic agent that bares nuclei of leukocytes and solubilizes platelets or erythrocytes is used to solubilize platelets or erythrocytes in a platelet preparation or an erythrocyte preparation.

DISCLOSURE OF THE INVENTION

The present invention has been accomplished in the light of the above circumstances. The object of the present invention is to provide a method and an apparatus for readily measuring leukocyte count in a platelet preparation or an erythrocyte preparation.

As a result of the present inventors' efforts to achieve the aforementioned object, they have been found that measurement of the leukocyte count can be facilitated and a measurement apparatus without requiring visual measurement can be obtained by utilizing a cytolytic agent that can bare nuclei of leukocytes and solubilize platelets or erythrocytes, because such a cytolytic agent can bare nuclei of leukocytes and solubilize platelets or erythrocytes when it is added to a platelet preparation solution or an erythrocyte preparation solution. Thus, the present invention has been accomplished.

That is, the present invention provides a method for counting leukocytes in a platelet preparation by staining the leukocytes, comprising adding a cytolytic agent capable of baring nuclei of leukocytes and solubilizing platelets to a solution of the platelet preparation to bare nuclei of the leukocytes and solubilize platelets in the solution of the platelet preparation.

In the present specification, terms "platelet preparation" and "solution of the platelet preparation" are used. As for these terms, if a platelet preparation is originally in the form of a solution, "platelet preparation" is equivalent to "solution of the platelet preparation". It is also contemplated that, even if a platelet preparation is in the form of a solid or the like, the preparation can be used as a solution after dissolution.

The present invention also provides a method for counting leukocytes in a platelet preparation by staining the leukocytes, comprising:

mixing and shaking a solution of the platelet preparation solution, a cytolytic agent capable of baring nuclei of leukocytes and solubilizing platelets and a dye, in an accumulation container comprising an opening, a sidewall portion and a bottom portion, a part or all of the sidewall portion having a horizontal sectional area gradually increasing in a direction from the bottom portion towards the opening, to solubilize platelets, bare nuclei of the leukocytes and stain the leukocytes, setting the accumulation container on a centrifuge to accumulate the stained leukocytes on the bottom portion of the accumulation container, and counting the stained leukocytes.

In measurement by baring nuclei of leukocytes and staining the leukocytes, what is actually measured is usually DNA aggregates of stained bared nuclei of individual leukocytes. In the present specification, the term "leukocytes" may be used to refer not only to leukocytes in the normal state, but also to the DNA aggregates of stained bared nuclei of leukocytes.

In the above method for counting leukocytes in the platelet preparation, the cytolytic agent added to the solution of the platelet preparation is preferably selected from the group consisting of anionic surfactants, cationic surfactants, amphoteric surfactants and nonionic surfactants. The amount of the cytolytic agent added to the solution of the platelet preparation solution is preferably 0.2 to 5% (w/v).

The present invention also provides a method for counting leukocytes in a platelet preparation by staining the leukocytes, comprising:

placing a solution of the platelet preparation in an accumulation container comprising an opening, a sidewall portion, and a bottom portion having a membrane filter through which leukocytes are impassable, a part or all of the sidewall portion having a horizontal sectional area gradually increasing in a direction from the bottom portion towards the opening, filtering the solution of the platelet preparation through the membrane filter provided at the bottom portion of the accumulation container containing the solution of the platelet preparation to accumulate the leukocytes on the bottom portion, adding a surfactant and a dye to the leukocytes accumulated on the bottom portion to bare nuclei of the leukocytes and stain the leukocytes, and counting the stained leukocytes.

The present invention also provides a method for counting leukocytes in an erythrocyte preparation by staining the leukocytes, comprising adding a cytolytic agent capable of baring nuclei of leukocytes and solubilizing erythrocytes to a solution of the erythrocyte preparation to bare nuclei of the leukocytes and solubilize erythrocytes in the solution of the erythrocyte preparation.

In the present specification, terms "erythrocyte preparation" and "solution of the erythrocyte preparation" are used. As for these terms, if an erythrocyte preparation is originally in the form of a solution, "erythrocyte preparation" is equivalent to "solution of the erythrocyte preparation". It is also contemplated that, even if an erythrocyte preparation is in the form of a solid, the preparation can be used as a solution after dissolution.

The present invention also provides a method for counting leukocytes in an erythrocyte preparation by staining the leukocytes, comprising:

mixing and shaking a solution of the erythrocyte preparation, a cytolytic agent capable of baring nuclei of leukocytes and solubilizing erythrocytes and a dye, in an accumulation container comprising an opening, a sidewall portion and a bottom portion, a part or all of the sidewall portion having a horizontal sectional area gradually increasing in a direction from the bottom portion towards the opening, to solubilize erythrocytes, bare nuclei of the leukocytes and stain the leukocytes, setting the accumulation container on a centrifuge to accumulate the stained leukocytes on the bottom portion of the accumulation container, and counting the stained leukocytes.

In the above method for counting leukocytes in the erythrocyte preparation, the cytolytic agent is preferably selected from the group consisting of anionic surfactants, cationic surfactants, amphoteric surfactants and nonionic surfactants. The amount of the cytolytic agent added to the solution of the erythrocyte preparation is preferably 0.1 to 10% (w/v).

The present invention also provides a leukocyte accumulation container comprising an opening, a bottom portion and a sidewall portion, a part or all of the sidewall portion having a horizontal sectional area gradually increasing in a direction from the bottom portion towards the opening. The present invention also provides such a leukocyte accumulation container wherein the bottom portion has a membrane filter through which leukocytes are impassable. The maximum diameter of the bottom portion of the accumulation container according to the present invention is preferably 0.2 to 5 mm. The maximum diameter of the bottom portion means the longest diameter irrespective of the shape of the bottom portion. For example, if the bottom portion has a circular shape, the diameter of the circle is the maximum diameter. If it has a quadrangular shape, the length of the diagonal is the maximum diameter.

The present invention also provides an apparatus for counting leukocytes comprising:

any one of the above leukocyte accumulation containers having an opening, a bottom portion and a sidewall portion, a part or all of the sidewall portion having a horizontal sectional area gradually increasing in a direction from the bottom portion towards the opening, a lens portion for projecting the state of the bottom portion of the leukocyte accumulation container as an image of which magnification can be changed by the lens portion, detection means for detecting the number of the leukocytes accumulated on the bottom portion of the leukocyte accumulation container by analyzing the image of the bottom portion of the leukocyte accumulation container projected via the lens portion, and output means for outputting detection results obtained by the detection means, wherein the detection means comprises an image-capturing portion having an image-capturing surface for capturing an image of the bottom portion of the leukocyte accumulation container projected via the lens portion, an image analysis processor that identifies leukocytes in the image of the bottom portion of the leukocyte accumulation container on the image-capturing surface and a counter for leukocyte count, and the bottom portion of the leukocyte accumulation container has a size such that the image of the entire bottom portion is in the image-capturing surface of the detection means as one image. The image-capturing portion preferably comprises CCD image-processing means.

The present invention will be described in detail below.

METHOD FOR COUNTING LEUKOCYTES IN PLATELET PREPARATION

Figure 1:
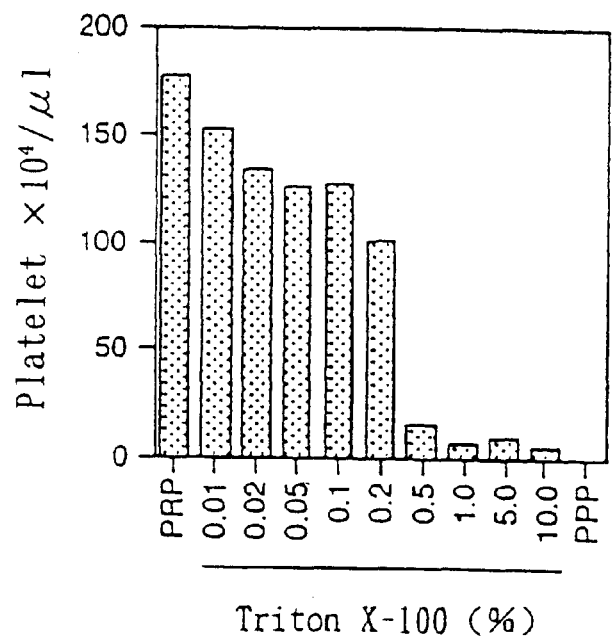
FIG. 1 shows the measurement results for platelet count in a platelet preparation at each concentration of added Triton X-100.

In the first method for counting leukocytes of the present invention, a cytolytic agent capable of baring nuclei of leukocytes and solubilizing platelets is added to a solution of the platelet preparation to bare nuclei of the leukocytes and solubilize platelets in the solution of the platelet preparation; a dye or the like is used to stain the leukocytes; and then leukocytes in the solution of the platelet preparation are counted. After adding the cytolytic agent, it is preferable to appropriately shake the solution of the platelet preparation so that the cytolytic agent is sufficiently diffused in the solution.

The cytolytic agent used in the method of the present invention is not particularly limited so long as it can bare nuclei of leukocytes and solubilize platelets. Specifically, however, examples thereof include anionic surfactants, cationic surfactants, amphoteric surfactants, nonionic surfactants, and so forth.

The above anionic surfactants include, specifically, sodium dodecylsulfate, sodium taurodeoxycholate, sodium deoxycholate, sodium tetradecylsulfate, sodium dodecylsulfonate, sodium tetradecylsulfonate, sodium cholate, sodium taurocholate and so forth. The above cationic surfactants include, specifically, cetyltrimethylammonium bromide, tetradecyltrimethylammonium chloride, dodecylpyridinium bromide, cetylpyrimidinium chloride and so forth. The above amphoteric surfactants include, specifically, CHAPS (3-[(3-cholamidopropyl) dimethylammonio]-propanesulfonate), CHAPSO (3-[(3-cholamidopropyl)dimethylammonio]-2-hydroxy-1-propanesulfonate), palmitoyl lysolecithin, dodecyl-N-betaine and so forth.

The above nonionic surfactants include, specifically, Triton X-100 (trade name), Nonidet P-40 (trade name), Igepal CA-630 (trade name), octylglucoside, Tween 20 (trade name), Tween 80 (trade name), Triton X-405 (trade name), dodecylglucoside, Sterox 67-K (trade name), Triton X-102 (trade name), heptylthioglucoside, decylglucoside, nonylthioglucoside, octylmaltoside, dodecylmaltoside, decanoyl-N-methylglucamide, polyoxyethylene dodecyl ether (for example, those commercially available with the trade names of Brij series, Lubrol W and AL series etc.), polyoxyethylene heptamethylhexyl ether (for example, those commercially available with the trade names of Nikkol BTD series etc.), polyoxyethylene isooctyl phenyl ether (for example, those commercially available with the trade names of Triton X series, Nikkol OP series etc.), polyoxyethylene nonyl phenyl ether (for example, those commercially available with the trade names of Triton N series, Nikkol NP series etc.), polyoxyethylene fatty acid ester (for example, those commercially available with trade names of Span series, Sterox CO series etc.), sucrose fatty acid ester, polyoxyethylene sorbitol ester (for example, those commercially available with the trade names of Tween series, Emasol series etc.) and so forth.

Among these surfactants, preferably used for the present invention as the cytolytic agent are sodium dodecylsulfate, sodium taurodeoxycholate, Triton X-100, Nonidet P-40, Igepal CA-630, octylglucoside, Tween 20 and so forth. More preferably, Triton X-100, Nonidet P-40, Igepal CA630 and so forth are used. Triton X-100 or the like is particularly preferred.

In the present invention, one or more cytolytic agents may be used.

The preferred amount of the cytolytic agent added to the solution of the platelet preparation (concentration of the cytolytic agent in the solution of the platelet preparation) can be determined by performing a preliminary experiment. Although it depends on the types of the platelet preparation and the cytolytic agent, the centrifugation conditions and so forth, the concentration of the cytolytic agent in the solution of the platelet preparation is preferably 0.2 to 5% (w/v), more preferably 0.5 to 4% (w/v) and particularly preferably 0.8 to 2% (w/v). At a concentration within this range, almost all the platelets are solubilized and the added cytolytic agent is rarely precipitated. Therefore, the solution of the platelet preparation shows excellent light transmittance. Furthermore, this range is within a range where nuclei of leukocytes can be bared to such an extent that sufficient staining and accurate leukocyte count are enabled.

According to the method of the present invention, accurate leukocyte count can be readily obtained even for a sample containing a small amount of leukocytes because platelets are solubilized so that leukocytes are unlikely to be covered with platelets.

When the cytolytic agent used for the present invention is used at a concentration within the above range suitable for solubilizing platelets, it can also bare nuclei of leukocytes. That is, the cytolytic agent can be used to bare nuclei of leukocytes and solubilize platelets in the solution of the platelet preparation.

After adding the cytolytic agent, it is preferable to stir the solution of the platelet preparation to bare nuclei of leukocytes and solubilize platelets. It is preferable to stir the solution for 5 seconds to 2 minutes, particularly preferably for 10 seconds to 1 minute, by using a stirrer generally used for measurement instruments. If stirring is performed for duration within this range, nuclei of leukocytes are sufficiently bared for staining and bared nuclei are rarely destroyed.

In the method of the present invention, leukocytes can be stained by a usual method. For example, a cytolytic agent capable of baring nuclei of leukocytes and solubilizing platelets is added to the solution of the platelet preparation; the mixture is stirred by using a stirrer to bare nuclei of leukocytes; and a dye is added thereto to stain bared nuclei of the leukocytes. Alternatively, both of the cytolytic agent and the dye can be added before the solution is stirred, which is encompassed by the method of the present invention. If the cytolytic agent and the dye are added at the same time, they may be separately added to the solution of the platelet preparation. However, it is preferable from a viewpoint of operability to add a mixture obtained by mixing the two reagents beforehand to the solution of the platelet preparation.

Preferred dyes for staining bared nuclei of leukocytes include cyanine, phenanthridine/acridine and indole/imidazole dyes. Specifically, propidium iodide, ethidium bromide and ethidium homodimer are preferred among the phenanthridine/acridine dyes. Hoechst 33258, Hoechst 33342, DAPI (4',6-diamidino-2-phenylindole), DIPI (4',6-

(diimidazolin-2-yl)-2-phenylindole) and so forth are preferred among the indole/imidazole dyes.

Further, detection of leukocytes by "staining" in the present invention includes detecting leukocytes by using "luminescence", "fluorescence" or the like, widely used in the immunoanalytical methods. For example, in order to detect and differentiate two types of leukocytes having different antigenic determinants, a first antibody-fluorochrome conjugate is prepared by binding a first fluorochrome with an antibody corresponding to an antigenic determinant specific to one type of leukocytes and a second antibody-fluorochrome conjugate is prepared by binding a second fluorochrome with an antibody corresponding to an antigenic determinant specific to the other type of leukocytes, and the conjugates are both added to a sample containing a plurality of types of leukocytes. The first antibody-fluorochrome conjugate and the second antibody-fluorochrome conjugate separately bind to leukocytes corresponding to each antibody. Leukocytes having each of two different antigenic determinants can be individually counted using fluorescence filters capable of differentially detecting each of the first fluorochrome and the second fluorochrome, for example. When the total leukocyte count in a measurement sample is measured, the number of leukocytes bound to neither the first antibody-fluorochrome conjugate nor the second antibody-fluorochrome conjugate can be also measured.

By utilizing the above first method for counting leukocytes, leukocytes in the solution of the platelet preparation can be counted in a simple manner through staining of the leukocytes. That is, the second method for counting leukocytes of the present invention is a method for counting leukocytes according to the above first method using an accumulation container comprising an opening, a sidewall portion and a bottom portion, a part or all of the sidewall portion having a horizontal sectional area gradually increasing in a direction from the bottom portion towards the opening.

Specifically, in the second method for counting leukocytes, the solution of the platelet preparation solution, the cytolytic agent capable of baring nuclei of leukocytes and solubilizing platelets and the dye are mixed in an accumulation container comprising an opening, a sidewall portion and a bottom portion, a part or all of the sidewall portion having a horizontal sectional area gradually increasing in a direction from the bottom portion towards the opening; then the resulting solution is shaken to solubilize platelets, bare nuclei of leukocytes and stain the leukocytes; the accumulation container is set on a centrifuge to accumulate the stained leukocyte nuclei at the bottom portion of the accumulation container; and the leukocyte nuclei are counted. As the accumulation container used here, a leukocyte accumulation container described below can be preferably used. Leukocytes may be stained at the same time as when nuclei of the leukocytes are bared as described above, or stained in a separate process after bared nuclei are obtained.

The third method for counting leukocytes is a method for counting leukocytes in a platelet preparation by staining the leukocytes, wherein platelets are removed by filtration using an accumulation container comprising an opening, a sidewall portion, and a bottom portion having a membrane filter through which leukocytes are impassable, a part or all of the sidewall portion having a horizontal sectional area gradually increasing in a direction from the bottom portion towards the opening, without requiring solubilization of platelets as an essential process.

That is, the third method for counting leukocytes is characterized by placing a solution of the platelet preparation in the aforementioned accumulation container of which bottom portion has the aforementioned membrane filter, filtrating the solution of the platelet preparation through the membrane filter at the bottom portion of the accumulation container containing the solution of the platelet preparation so that leukocytes are accumulated on the bottom portion, adding a surfactant and a dye to the leukocytes accumulated at bottom portion to bare nuclei of the leukocytes and stain them, and counting the leukocyte nuclei. As the accumulation container, a leukocyte accumulation container of the present invention described below can be preferably used. If a platelet preparation is used as a sample, any membrane filter through which platelets are passable and leukocytes are impassable can be used at the bottom portion of the accumulation container. Preferably, the pore size is about 3 to 7 $\mu$m, particularly preferably about 4 to 6 $\mu$m.

In the third method for counting leukocytes, it is sufficient that nuclei of leukocytes can be bared and stained with the surfactant and the dye, and it can be attained by a usual method. For example, as the surfactant, surfactants of Span, Arlacel, Tween, Triton series and so forth can be used at a usual concentration for baring nuclei of leukocytes. In the third method for counting leukocytes, the aforementioned cytolytic agent capable of baring nuclei of leukocytes and solubilizing platelets can be used instead of the surfactant. It should be understood that such an embodiment is also encompassed by the third method for counting leukocytes of the present invention.

If leukocytes are accumulated on the bottom portion of the above accumulation container without solubilizing or separating and removing platelets by filtration, leukocytes are embedded in many platelets present in the solution of the platelet preparation, which makes it difficult to detect the leukocytes. However, platelets are solubilized using the first method for counting leukocytes, or the platelets can be removed by filtration. Therefore, even if a leukocyte accumulation container having the bottom portion of a small area is used to accumulate leukocytes at the bottom portion of the container, leukocytes are unlikely to be embedded in the platelets. Thus, leukocytes can be detected in a small area, and thereby labor required for the detection will be reduced.

Detection of the leukocytes that are accumulated on the bottom portion and stained can be performed by, for example, a usual method such as visual measurement by the observer using a microscope. However, apparatuses for counting leukocytes and the above leukocyte accumulation containers suitable for practicing the above methods will be described in detail below.

Method for Counting Leukocytes in Erythrocyte Preparation

Using methods and apparatuses similar to those for the platelet preparation described above, leukocytes present in an erythrocyte preparation can be counted by solubilizing erythrocytes, baring nuclei of leukocytes and staining them. When the leukocyte count in the erythrocyte preparation is measured, a cytolytic agent to be added to a solution of the erythrocyte preparation is one that can bare nuclei of leukocytes and solubilize erythrocytes. Specific examples and preferred examples thereof are similar to those described for the above cytolytic agent capable of baring nuclei of leukocytes and solubilizing platelets. For the case where leukocytes in the erythrocyte preparation are counted, a preferred concentration of the cytolytic agent added to the solution of the erythrocyte preparation is as follows.

The preferred amount of the cytolytic agent added to the solution of the erythrocyte preparation (concentration of the cytolytic agent in the solution of the erythrocyte preparation) can also be determined by performing a preliminary experiment. Although it depends on types of the erythrocyte preparation and the cytolytic agent, the centrifugation conditions and so forth, the concentration of the cytolytic agent in the solution of the erythrocyte preparation is preferably 0.1 to 10% (w/v), more preferably 0.2 to 5% (w/v), particularly preferably 0.5 to 3% (w/v). At a concentration within this range, almost all the erythrocytes are solubilized and the added cytolytic agent is rarely precipitated. Therefore, the solution of the erythrocyte preparation has excellent light transmittance. Furthermore, within this range, nuclei of leukocytes are sufficiently bared to such an extent that sufficient staining and accurate leukocyte count measurement are enabled.

Leukocyte Accumulation Container and Apparatus for Counting Leukocytes of the Present Invention The apparatus for counting leukocytes of the present invention (also referred to as "measurement apparatus of the present invention" hereafter) comprises:
(1) a leukocyte accumulation container comprising an opening, a bottom portion and a sidewall portion, a part or all of the sidewall portion having a horizontal sectional area gradually increasing in a direction from the bottom portion towards the opening,
(2) a lens portion for projecting the state of the bottom portion of the leukocyte accumulation container as an image of which magnification can be changed by the lens portion,
(3) detection means for detecting the number of the leukocytes accumulated at the bottom portion of the leukocyte accumulation container by analyzing the image of the bottom portion of the leukocyte accumulation container projected via the lens portion, and
(4) output means for outputting detection results obtained by the detection means, wherein said detection means comprises:
(5) an image-capturing portion having an image-capturing surface for capturing an image of the bottom portion of the leukocyte accumulation container projected via the lens portion,
(6) an image analysis processor for identifying leukocytes from the image of the bottom portion of the leukocyte accumulation container on the image-capturing surface, and
(7) a counter for leukocyte count, and
(8) said bottom portion of the leukocyte accumulation container has a size such that the image of the entire bottom portion is in the image-capturing surface of the detection means as one image.

The above apparatus for counting leukocytes uses the leukocyte accumulation container of the present invention comprising an opening, a bottom portion and a sidewall portion, a part or all of the sidewall portion having a horizontal sectional area gradually increasing in a direction from the bottom portion towards the opening (hereafter, the leukocyte accumulation container of the present invention may be referred to as the "container of the present invention"). This leukocyte accumulation container of the present invention will be described first with reference to FIGS. 4 to 12.

<1>Leukocyte Accumulation Container of the Present Invention

The container of the present invention is used to accumulate leukocytes at bottom portion thereof by centrifugation or the like and comprises a bottom portion, a sidewall portion and an opening. The shape of the bottom portion is not particularly limited. For example, it may be in a circular shape, quadrangular shape or the like. However, when the container is attached to an apparatus for counting leukocytes of the present invention, it is preferable that the shape of the bottom portion is similar to that of an image-capturing surface possessed by the apparatus for counting leukocytes. Although the maximum diameter of the bottom portion depends on the size of the image-capturing surface contained in the apparatus for counting leukocytes as described below, it is preferably 0.2 to 5 mm, particularly preferably 1 to 3 mm. The maximum diameter of the bottom portion is the longest diameter of the bottom portion irrespective of the shape. For example, if the bottom portion has a circular shape like the leukocyte accumulation container (1) shown in FIGS. 4 to 6, the diameter of the circle is the maximum diameter. If it has a quadrangular shape like the individual sample solution reservoir (10) in the leukocyte accumulation container (1A) shown in FIGS. 7 to 9 below, the length of the diagonal is the maximum diameter.

The bottom portion can have a membrane filter through which leukocytes are impassable so that leukocytes can be accumulated at the bottom portion by filtration. The leukocyte accumulation container using a membrane filter is more favorably used to count leukocytes in a platelet preparation.

The shape of the opening is not particularly limited, either. The maximum diameter is preferably 2 to 20 mm, particularly preferably 3 to 15 mm.

A container of the present invention has a sidewall portion a part or all of which has a horizontal sectional area gradually increasing in a direction from the bottom portion towards the opening (hereafter, this portion may be referred to as "tapered portion"). Since the tapered portion is provided, a sample solution of an amount sufficient for the measurement can be placed in the container even if a sample solution contains a small amount of leukocytes like a solution of the platelet preparation or the like and the bottom portion of the container has a small preferred diameter as described above. When leukocytes are accumulated by centrifugation, the leukocytes can substantially be accumulated on the bottom portion by one centrifugation although it depends on centrifugation conditions, and thereby the measurement can be made to be easy.

The tapered portion may constitute all or a part of the sidewall portion. Preferably, the tapered portion is provided from the portion adjacent to the bottom portion, or a portion which has a constant horizontal sectional area is provided from the portion adjacent to the bottom portion and the tapered portion is provided thereon, for example. More specifically, there can be mentioned a tapered portion that is provided so as to constitute all of the sidewall portion like the container shown in FIGS. 4 to 6, a tapered portion that is provided from the bottom portion on which a portion that has a constant horizontal sectional area is provided like the container (sample solution reservoir) shown in FIGS. 7 to 9 and so forth. Furthermore, there can also mentioned a tapered portion provided on a portion which has a constant horizontal sectional area and is provided from the portion adjacent to the bottom portion as in the container shown in FIGS. 10 to 12 and so forth.

To form a container of the present invention, usual materials can be used. When leukocytes are measured from below, a transparent material is preferred. Preferably, polystyrene resin, glass and acrylic resin, particularly preferably, polystyrene resin and so forth are mentioned as such materials.

The container of the present invention is used with covering the opening with a sheet or the like having an adhesive portion to place a lid on the opening, as required.

Figure 4:
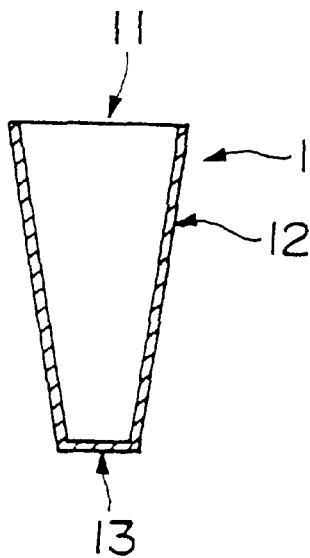
FIG. 4 shows a front sectional view of an example of the leukocyte accumulation container of the present invention.
Figure 5:
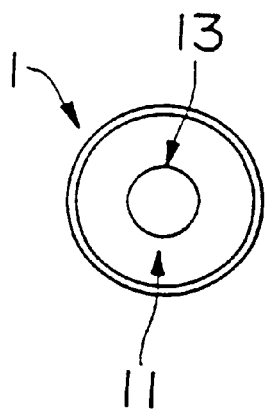
FIG. 5 shows a plane view of an example of the leukocyte accumulation container of the present invention.
Figure 6:
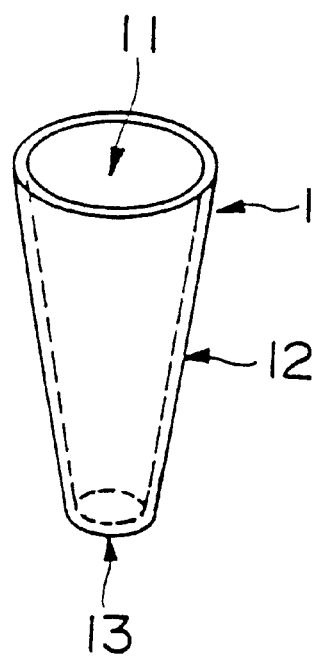
FIG. 6 is a perspective view of an example of the leukocyte accumulation container of the present invention.

FIGS. 4 to 6 show an example of the leukocyte accumulation container of the present invention (also referred to as a "container of Embodiment 1" hereafter). FIG. 4 shows a front sectional view of the leukocyte accumulation container of the present invention. FIG. 5 shows a plane view of the leukocyte accumulation container of the present invention. FIG. 6 shows a perspective view of the leukocyte accumulation container of the present invention.

The container (1) of Embodiment 1 has a circular opening (11), a circular bottom portion (13) and a sidewall portion (12) all of which constitutes a tapered portion. The bottom portion has a diameter of 3 mm, and the opening has a diameter of 10 mm. The height is 20 mm. Since the container is formed with a polystyrene resin and transparent, accumulated leukocytes can be seen through the bottom portion.

Figure 7:
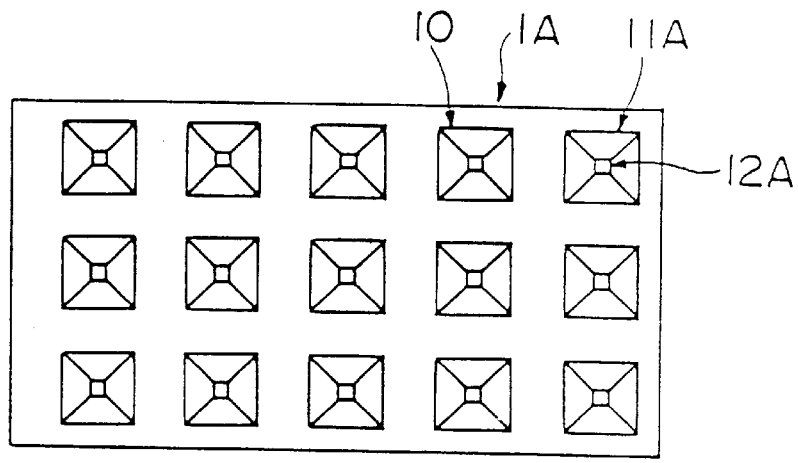
FIG. 7 is a plane view of an example of the collective type leukocyte accumulation container of the present invention.
Figure 8:
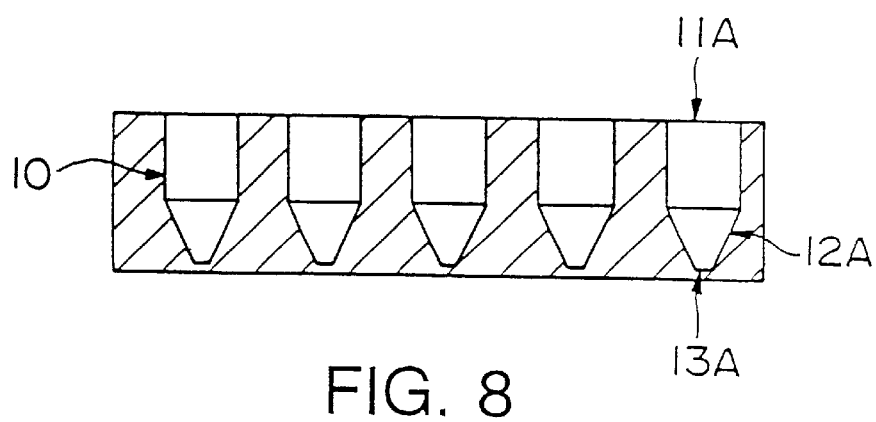
FIG. 8 is a front sectional view of an example of the collective type leukocyte accumulation container of the present invention.
Figure 9:
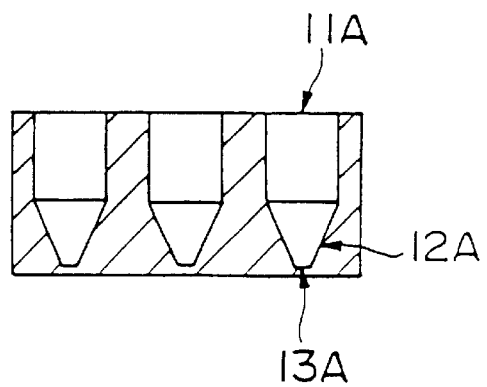
FIG. 9 is a sectional side view of an example of the collective type leukocyte accumulation container of the present invention.

FIGS. 7 to 9 show another example of the leukocyte accumulation container of the present invention (also referred to as a "container of Embodiment 1A" hereafter). FIG. 7 is a plane view of the example of the collective type leukocyte accumulation container of the present invention. FIG. 8 is a front sectional view of the example of the collective type leukocyte accumulation container of the present invention. FIG. 9 is a sectional side view of the example of the collective type container of the collective type leukocyte accumulation container of the present invention.

The container (1A) of Embodiment 1A is a collective type leukocyte accumulation container having a plurality of sample solution reservoirs (10). Each sample solution reservoir (10) is a container for storing each sample solution. The sample solution reservoir (10) has a square shaped bottom portion (13A) and a square shaped opening (11A). A tapered portion is provided from a portion of the sidewall portion (12A) adjacent to the bottom portion. Furthermore, a portion that has a constant horizontal sectional area is provided on the tapered portion.

The container of Embodiment 1A has a length of 48 mm, width of 88 mm and height of 22 mm. The maximum diameter of the bottom portion (diagonal of the square bottom portion) of the sample solution reservoir is about 2.8 mm. The same material as used for the container of Embodiment 1 is used.

A bucket that can accommodate the container of Embodiment 1A can be used to set the container on a centrifuge. The bucket may be one generally used for setting a collective type container similar to a container of Embodiment 1A on a centrifuge.

Figure 10:
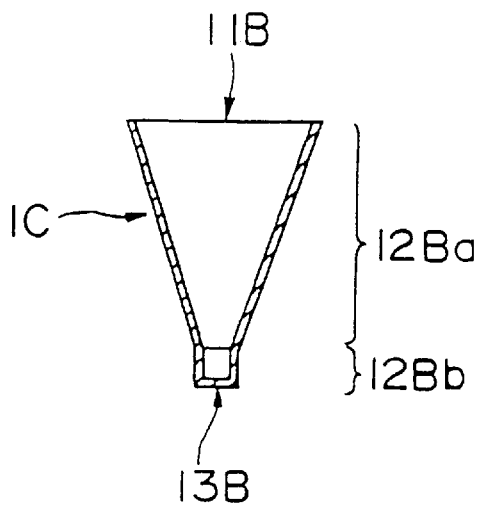
FIG. 10 is a front sectional view of another example of the leukocyte accumulation container of the present invention.
Figure 11:
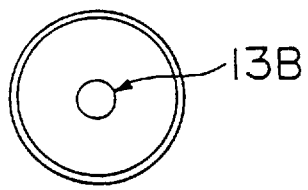
FIG. 11 is a plane view of another example of the leukocyte accumulation container of the present invention.
Figure 12:
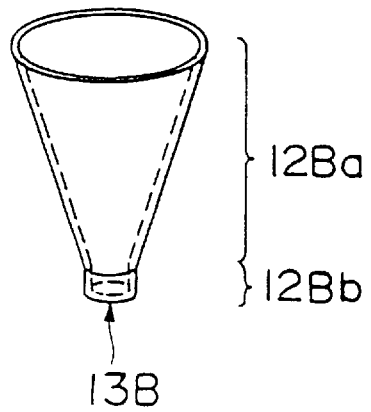
FIG. 12 is a perspective view of another example of the leukocyte accumulation container of the present invention.

FIGS. 10 to 12 show a further example of the leukocyte accumulation container of the present invention (also referred to as "container of Embodiment 1C" hereafter). FIG. 10 is a front sectional view of the further example of the leukocyte accumulation container of the present invention. FIG. 11 is a plane view of the further example of the leukocyte accumulation container of the present invention. FIG. 12 is a perspective view of the further example of the leukocyte accumulation container of the present invention.

The container (1C) of Embodiment 1C has a sidewall portion consisting of a tapered portion (12Ba) and a cylindrical portion (12Bb). The cylindrical portion of Embodiment 1C is connected to the periphery of the bottom portion (13B) and have a constant horizontal sectional area. The tapered portion (12Ba) is provided on the cylindrical portion up to the opening (11B).

<2>Apparatus for Counting Leukocytes of Present Invention

The apparatus for counting leukocytes of the present invention is an apparatus for detecting leukocytes accumulated at the bottom portion of the above leukocyte accumulation container of the present invention and counting the leukocytes.

In an apparatus for counting leukocytes of the present invention, the state of the bottom portion of the leukocyte accumulation container is projected as an image via a lens portion by which the magnification of the obtained image can be changed and the obtained image is captured by detection means having an image-capturing surface. That is, any lens portion can be used that can project the state of the bottom portion of the leukocyte accumulation container as an image and has the magnification that can change the size of the image of the bottom portion on the image-capturing surface of the detection means to a size in which leukocytes can be identified by the detection means and the number can be counted. Preferably, the magnification of 1 to 10 is used. Any lens portion usually used to change the magnification of an image in measurement instruments can be used so long as that can change the magnification of the image as described above. A plurality of lenses may be used although only one lens is illustrated in the examples shown in FIGS. 15 and 16 for simply representing the systems and the principles of the measurement instruments.

The detection means comprises an image-capturing portion having an image-capturing surface, an image analysis processor for identifying leukocytes in the image of the bottom portion of the leukocyte accumulation container on the image-capturing surface and a counter for leukocyte count.

The image-capturing portion captures an image of the bottom portion. The image-capturing surface provided on the image-capturing portion has a size such that the image of the entire bottom portion projected via the lens is within one field. For this purpose, it is contemplated that the size of the bottom portion, the magnification of the lens and the size of the image-capturing surface, or a combination thereof are adjusted. In the present invention, the size of the image-capturing surface can be set within the range generally used for measurement instruments by using the above leukocyte accumulation container of the present invention.

It is preferable that the image-capturing portion comprises CCD image-processing means, in view of connection with an image analysis processor or the like described below.

The leukocytes projected on the image-capturing surface of the imaging section are identified by an image analysis processor. Any image analysis processor can be used so long as it can identify stained leukocytes, that is, there can be used an image analysis processor that can identify fluorochrome, fluorescence substance, luminescence substance and so forth, which are used for staining leukocytes. The leukocytes identified by the image analysis processor is counted by the leukocyte counter.

The measured leukocyte count is output from the output means. Any output means can be used that allows a measurer to recognize the leukocyte count. Usual means such as a printer or an image display by a monitor can be used.

An instrument or apparatus generally used as an optical measurement instrument may be connected to the measurement apparatus of the present invention. For example, it can have a light source for lighting the observed surface to project an image on the image-capturing surface such as a xenon lamp, a YAG laser (532 nm), a halogen lamp, a metal halide lamp or an ultra high-pressure mercury lamp, a filter that transmit only a specific wavelength such as excitation light filter and fluorescence filter, a dichroic mirror and so forth.

In the apparatus for counting leukocytes of the present invention, leukocytes are accumulated on the bottom portion of the leukocyte accumulation container and can be detected within a small area. If the bottom portion of the container to be observed is not in the image-capturing surface as one image, the entire bottom portion must be scanned by moving the lens portion or the like. However, this operation is not necessary for the measurement apparatus of the present invention. Therefore, there can be provided a simple measurement apparatus that does not require a system or a program for integrating a plurality of images scanned by the lens or the like.

The apparatus for counting leukocytes of the present invention is suitable for practicing the above methods for counting leukocytes of the present invention, and enables mechanization of the leukocyte count in the solution of the platelet preparation or the solution of the erythrocyte preparation. Therefore, it enables to perform the measurement in a simple manner. The leukocyte count can also be automatized using the mechanized measurement apparatus. Samples that can be measured using the apparatus for counting leukocytes of the present invention are not limited to a platelet preparation and an erythrocyte preparation, but leukocyte counts in other blood preparations can also be measured using it.

Figure 15:
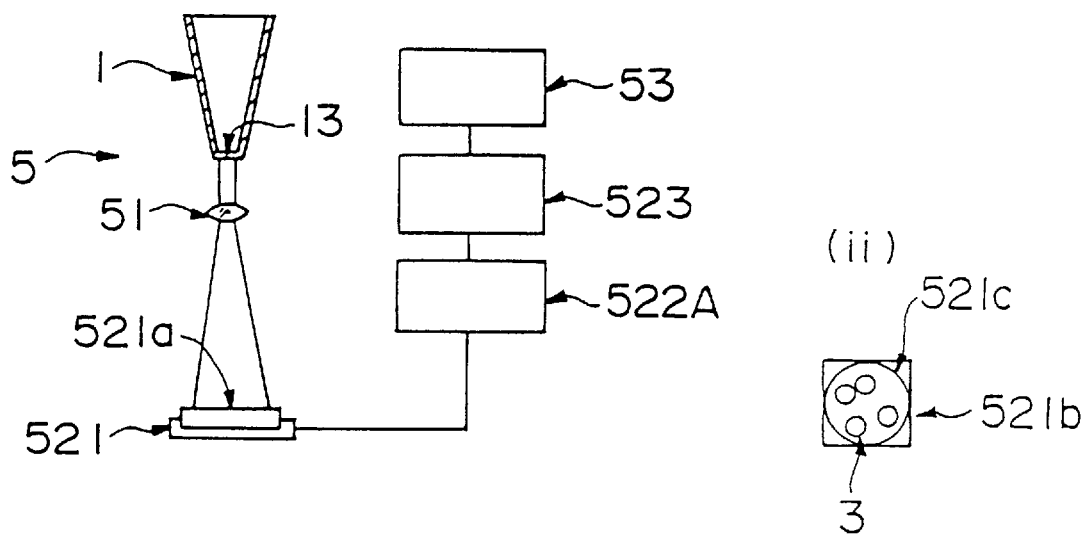
FIG. 15 shows principle of an example of the apparatus for counting leukocytes of the present invention. (i) shows the entire measurement apparatus, and (ii) shows an image on the image-capturing surface.

The apparatus for counting leukocytes of the present invention will be described below with reference to FIGS. 15 to 17. FIG. 15 shows the principle of an example of the apparatus for counting leukocytes of the present invention. FIG. 15 (i) shows the entire measurement apparatus (5), and (ii) shows an image on the image-capturing surface.

Accumulated leukocytes (3) are present at the bottom portion (13) of the leukocyte accumulation container (1). The entire bottom portion is enlarged via a lens portion (51) and projected on the image-capturing surface (521a) as an image. On an image-capturing surface (521a), the entire bottom portion of the leukocyte accumulation container (1), which is a field to be observed (521c), is captured as one image (521b). A CCD image processor (521) converts the image (521b) captured on the image-capturing surface (521a) to electrical signals and transmits them to an image analysis processor (522A). In the image analysis processor (522A), stained leukocyte (3) in the transmitted image are identified. The number of the identified leukocytes (3) is counted by a leukocyte counter (523) and the total count is obtained. The total count of the leukocytes (3) on the image is output by an output printer (53).

Figure 16:
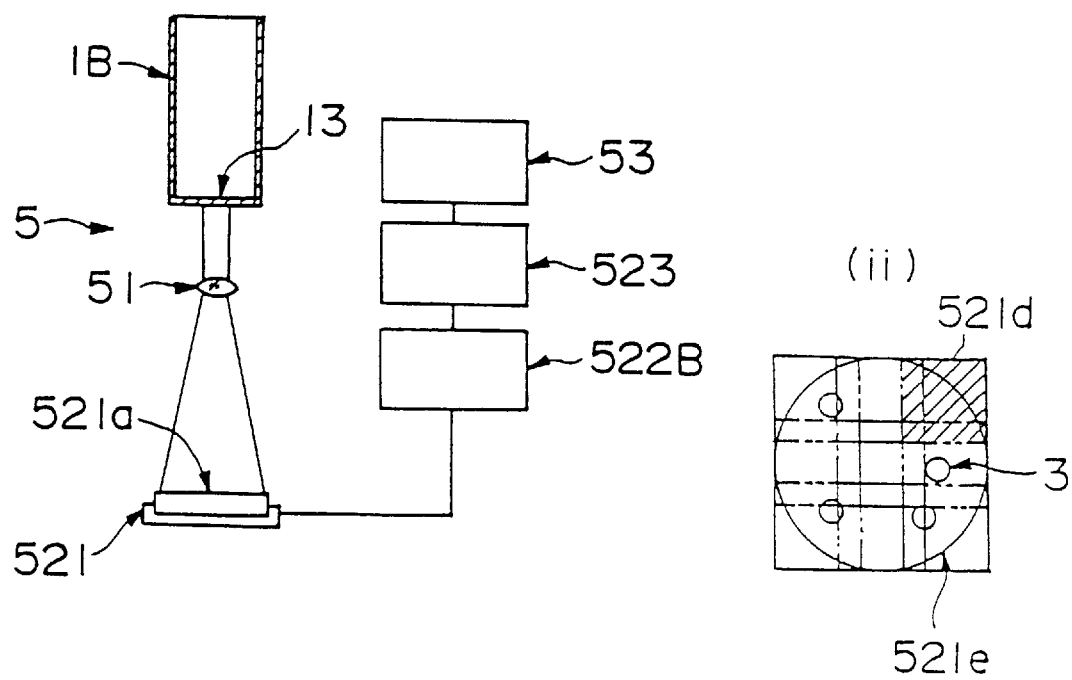
FIG. 16 shows principle of a comparative example of an apparatus for counting leukocytes. (i) shows the entire measurement apparatus, and (ii) shows an image on the image-capturing surface.

FIG. 16 (i) shows the principle of a comparative example of the apparatus for counting leukocytes. FIG. 16 (ii) shows the imaging area in the bottom portion of the leukocyte accumulation container that can be projected on the image-capturing surface. Differences compared with the apparatus for counting leukocytes shown in FIG. 15 will be mainly described below. In the apparatus for counting leukocytes shown in FIG. 16, the entire image of the bottom portion cannot be captured by the lens portion (51). Only the hatched part (521d) in (ii) can be captured as one image. Therefore, in order to detect the leukocytes from the entire bottom portion of the leukocyte accumulation container (1B), which is a field to be observed (521e), the bottom portion must be scanned by the lens portion to obtain a plurality of images and integrate them to measure the total count of the leukocytes. Therefore, the apparatus for counting leukocytes of the comparative example comprises a built-in image-integrating program in the image analysis processor (522B). Such a program is not essential for the apparatus for counting leukocytes of the present invention.

Figure 17:
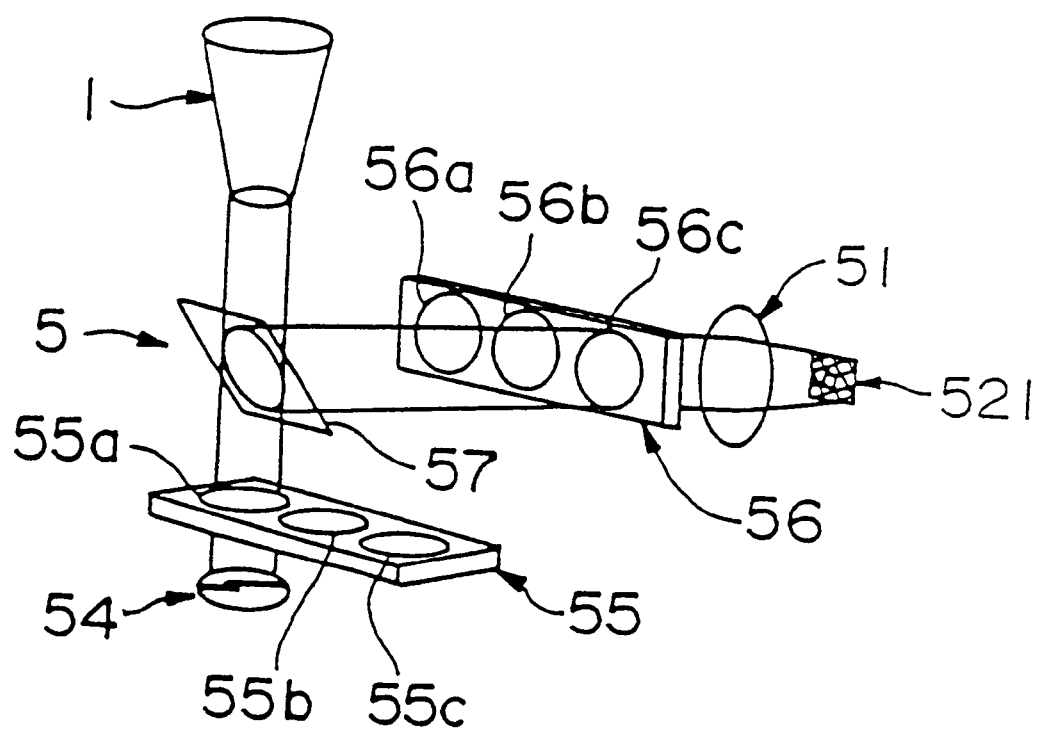
FIG. 17 shows the principle of another example of the apparatus for counting leukocytes of the present invention.

FIG. 17 shows the principle of another embodiment of the apparatus for counting leukocytes of the present invention. For the apparatus for counting leukocytes shown in FIG. 17, the same numbers are given to the same items in the apparatus for counting leukocytes of the present invention shown in FIG. 15, and only differences will be described.

In the apparatus for counting leukocytes (5) shown in FIG. 17, a light source (54) is provided below the leukocyte accumulation container (5). An excitation light filter slider (55) having three kinds of excitation light filters (55a, 55b and 55c) is provided between the light source (54) and the bottom portion of the leukocyte accumulation container (5). Since the excitation light filter slider (55) is disposed between the light source (54) and the bottom portion, any one of the excitation filters can be selected by sliding the excitation light filter slider.

A dichroic mirror (57) is further provided above the excitation light filter slider (55). The light selected by the excitation light filter is transmitted through the dichroic mirror (57) and irradiated on the observed surface. The generated fluorescence is reflected by the dichroic mirror (57), transmitted through the fluorescence filter (56a, 56b or 56c) and projected on the imaging section of the CCD image processing means (521) via the lens portion (51). Any one of the three kinds of fluorescence filters can be selected by sliding the fluorescence filter slider (56).

The apparatus for counting leukocytes shown in FIG. 17 can readily measure the number of the leukocytes selectively stained with different fluorochromes by selecting appropriate ones from three kinds for each of excitation light filters (55a, 55b and 55c) and fluorescence filters (56a, 56b and 56c).

BEST MODE FOR CARRYING OUT THE INVENTION

Examples of the present invention will be described below.

EXAMPLE 1

Leukocyte Count in Platelet Preparation

<1>Solubilization of Platelets in Solution of Platelet Preparation

15 $\mu$L of Triton X-100 surfactant was added to a solution of a platelet preparation at various concentrations so that the final concentration was 0.01 to 10%. Each solution of the platelet preparation to which Triton X-100 was added was stirred by a vortex mixer (Scientific Industry) for 20 seconds to accelerate baring nuclei of leukocytes, and the platelet count in the solution of the platelet preparation was measured by an automatic hemacytometer (Sysmex (trade name), Toa Medical Electronics Co., Ltd.) to evaluate the a solubilization of platelets by Triton X-100. At the same time, the light transmittance of the solution of the platelet preparation was measured by a spectrophotometer (Beckman).

Figure 2:
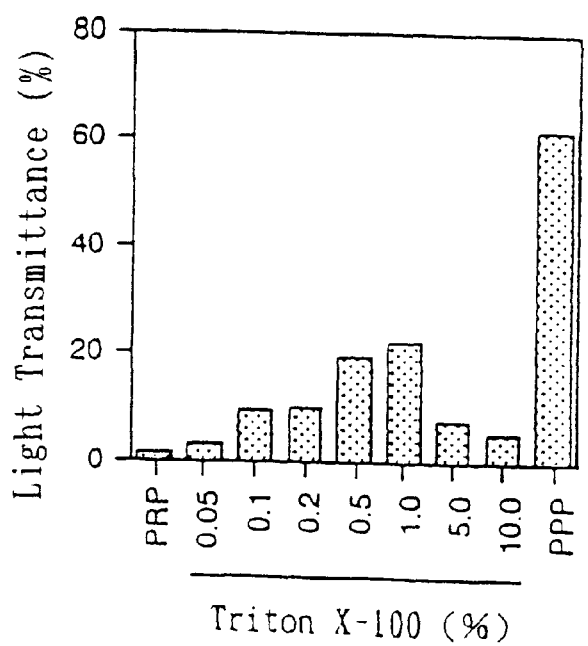
FIG. 2 shows light transmittance of a solution of a platelet preparation at each concentration of added Triton X-100.

The measurement results for the platelet count in the solution of he platelet preparation and the light transmittance are shown in FIGS. 1 and 2. In FIGS. 1 and 2, PRP and PPP represent platelet rich plasma and platelet poor plasma, respectively.

As shown in FIG. 1, it was revealed that the platelet count in the solution of the platelet preparation decreased depending on the concentration of Triton X-100 and that the platelets were solubilized depending on the concentration of Triton X-100. It was revealed, in particular, that most of platelets were solubilized when the concentration of Triton X-100 was higher than 0.2%.

As shown in FIG. 2, it was revealed that the light transmittance of the sample increased with the increase in the concentration of Triton X-100 up to the concentration of Triton X-100 of 1%, but the solution of the platelet preparation began to show turbidity due to deposition of Triton X-100, and the light transmittance was lowered when the concentration exceeded 1%.

Figure 13:
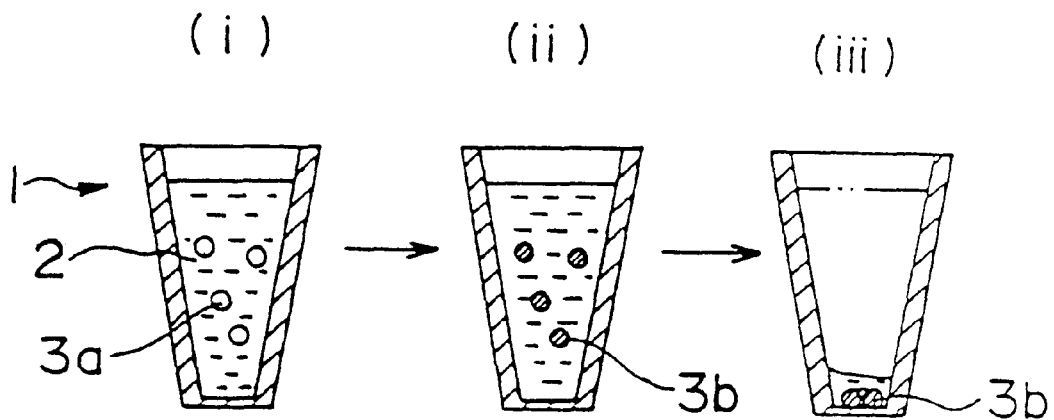
FIG. 13 shows the process of accumulation of leukocytes in a solution of a platelet preparation using the leukocyte accumulation container of the present invention from a point before the accumulation to a point after the accumulation. There are provided front sectional views of the leukocyte accumulation container. (i) shows the state before the accumulation, (ii) shows the state after nuclei of the leukocytes are bared and stained and platelets are solubilized, and (iii) shows the state after the accumulation.

<2>Leukocyte Count in Solution of Platelet Preparation (1) Method of Accumulating Stained Leukocytes by Centrifugation As shown in FIG. 13, 0.45 ml of platelet preparation (2), 0.05 ml of Triton X-100 at a concentration of 10% and 0.015 ml of propidium iodide at a concentration of 1 mM were added to the above container of Embodiment 1 (FIGS. 4 to 6) and stirred by a vortex mixer for 20 seconds so that platelets were dissolved and nuclei of leukocytes were bared and stained. In FIG. 13, 3$a$ and 3$b$ show leukocytes before nuclei thereof were bared and stained and leukocytes after nuclei thereof were bared and stained, respectively. The accumulation container was set on a centrifuge (Tomy Seiko Co., Ltd., Model LC06-SP) for 5 minutes to accumulate stained leukocytes.

The container where leukocytes were accumulated on the bottom portion was set on the apparatus for counting leukocytes provided with a CCD image processor to detect leukocytes accumulated on the bottom portion by the CCD image processor and measure the leukocyte count. The image of the bottom portion of the container of Embodiment 1 could be within the image-capturing surface of the CCD image processor as one image. Therefore, the image-capturing surface or the like did not need to be scanned.

Figure 14:
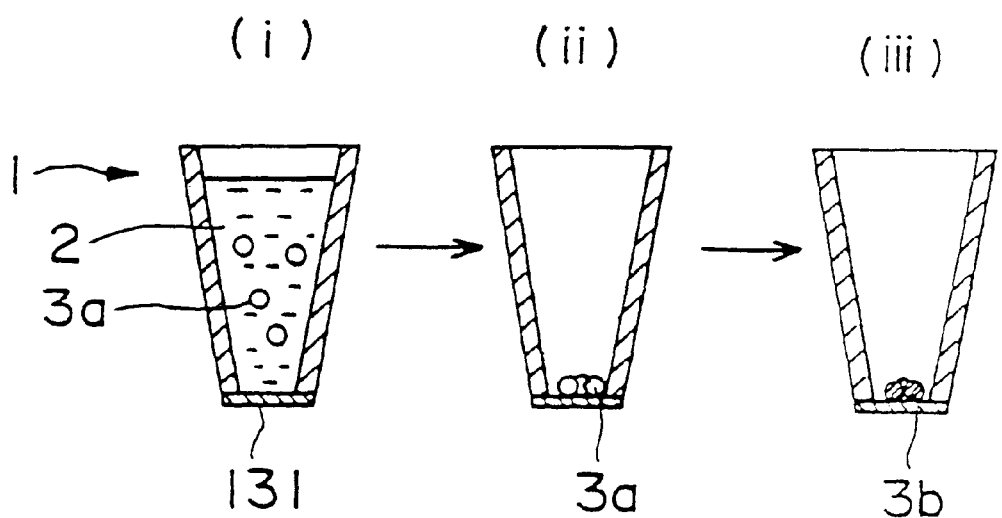
FIG. 14 shows the process of accumulation of leukocytes in a solution of a platelet preparation by using the leukocyte accumulation container of the present invention provided with a membrane filter at the bottom portion from a point before the accumulation to a point after the accumulation. There are provided front sectional views of the leukocyte accumulation container. (i) shows the state before the accumulation, (ii) shows the state after the accumulation by filtration, and (iii) shows the state after nuclei of the leukocytes are bared and stained.

(2) Method for Accumulating Leukocytes by Filtration, Baring Nuclei and Staining Them As shown in FIG. 14, 0.5 ml of platelet preparation (2) was placed in the container similar to Embodiment 1 except that the bottom portion consisted of a membrane filter (131), and leukocytes were accumulated on the bottom portion by suction filtration. 0.1 ml Triton X-100 at a concentration of 1.0% and 0.003 ml propidium iodide at a concentration of 1 mM were added so that nuclei of the leukocytes were bared and stained. The numerals 3$a$ and 3$b$ represent the same items as in the aforementioned FIG. 13.

The container where leukocytes were accumulated on the filter was set on an apparatus for counting leukocytes provided with a CCD image processor to detect the leukocytes accumulated on the bottom portion by the CCD image processor and measure the leukocyte count. The image of the bottom portion of the container of Embodiment 1 could be within the image-capturing surface of the CCD image processor as one image. Therefore, the image-capturing surface or the like did not need to be scanned.

EXAMPLE 2

Leukocyte Count in Erythrocyte Preparation

<1>Solubilization of Erythrocytes in Erythrocyte Preparation

15 $\mu$L of a surfactant, Triton X-100, was added to a solution of an erythrocyte preparation at various concentrations so that the final concentration was 0.01 to 10%. Each solution of the erythrocyte preparation to which Triton X-100 was added was stirred by a vortex mixer (Scientific Industry) for 20 seconds to accelerate baring nuclei of the leukocytes, and the erythrocyte count in the solution of the erythrocyte preparation was measured by an automatic hemacytometer (Sysmex (trade name), Toa Medical Electronics Co., Ltd.) to evaluate the solubilization of erythrocytes by Triton X-100. At the same time, bared nuclei of the leukocytes (leukocyte nuclei) were counted by a flow cytometer (Coulter, Model EICS XL).

Figure 3:
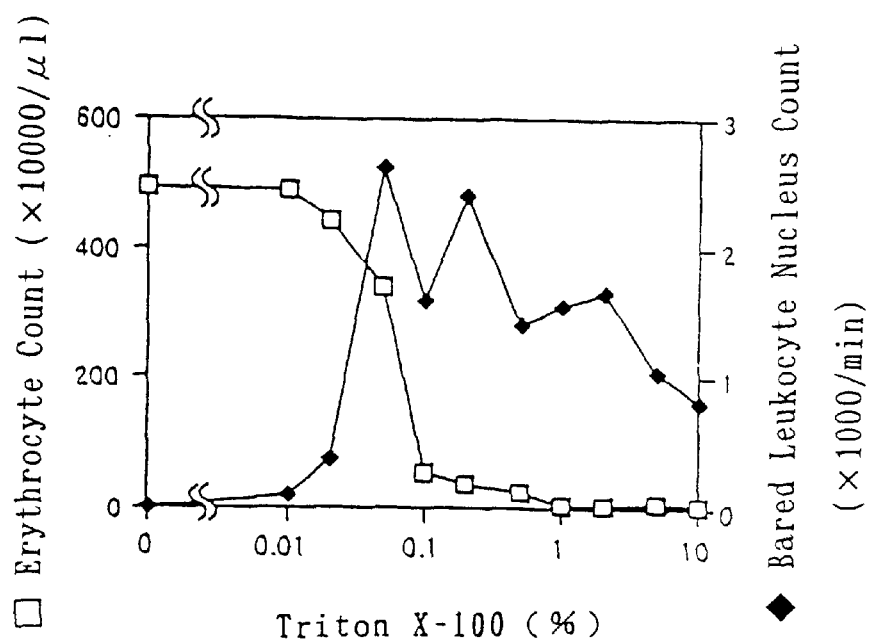
FIG. 3 shows the measurement results for erythrocyte count in an erythrocyte preparation and the measurement results for the bared leukocyte nucleus count by a flow cytometer at each concentration of added Triton X-100.

The measurement results for the erythrocyte count and the bared leukocyte nucleus count in the solution of the erythrocyte preparation are shown in FIG. 3.

<2>Leukocyte Count in Solution of Erythrocyte Preparation

87 $\mu$L of an erythrocyte preparation, 10 $\mu$L of Triton X-100 at a concentration of 10% and 3 $\mu$L of propidium iodide at a concentration of 1 mM were added to a container of the above Embodiment 1 (FIGS. 4 to 6) and stirred by a vortex mixer for 20 seconds so that erythrocytes were dissolved and nuclei of leukocytes were bared and stained. The accumulation, container was set on a centrifuge (Tomy Seiko Co., Ltd., Model LC06-SP) for 5 minutes to accumulate the stained leukocytes (corresponding to a case where the numeral 2 in FIG. 13 indicates an erythrocyte preparation).

The container where leukocytes were accumulated on the bottom portion was set on an apparatus for counting leukocytes provided with a CCD image processor to detect the leukocytes accumulated on the bottom portion by the CCD image processor and measure the leukocyte count. The image of the bottom portion of the container of Embodiment 1 can be within the image-capturing surface of the CCD image processor as one image. Therefore, the image-capturing surface or the like does not need to be scanned.

The results of the measurement revealed that the leukocyte count in a bag of erythrocyte preparation (200 ml) used as a sample was $2 \times 10^7$.

Industrial Applicability

According to the method for counting leukocytes of the present invention, even if a sample contains a small amount of leukocytes, the leukocytes are unlikely to be covered with platelets or erythrocytes because platelets or erythrocytes are solubilized, and thus accurate and easy measurement of the leukocyte count can be enabled. In particular, since leukocytes can be detected within a small area by using the leukocyte accumulation container of the present invention, labor required for the measurement can be reduced. In addition, the apparatus for counting leukocytes of the present invention can be constituted by a simple system. The apparatus for counting leukocytes of the present invention allows mechanized measurement of the leukocyte count and also enables automatic measurement.

What is claimed is:

1. A method for counting leukocytes in a platelet preparation by staining the leukocytes, comprising:

mixing and shaking a solution of the platelet preparation, a cytolytic agent capable of baring nuclei of leukocytes and solubilizing platelets, and a dye, in an accumulation container comprising an opening, a sidewall portion and a flat bottom portion, a part or all of the sidewall portion having a horizontal sectional area gradually increasing in a direction from the flat bottom portion towards the opening, to solubilize platelets, bare nuclei of the leukocytes and stain the leukocytes, centrifuging the accumulation container to accumulate the stained leukocytes on the flat bottom portion of the accumulation container, and counting the stained leukocytes.

2. The method for counting leukocytes according to claim 1, wherein the cytolytic agent is selected from the group consisting of anionic surfactants, cationic surfactants, amphoteric surfactants and nonionic surfactants.

3. The method for counting leukocytes according to claim 1, wherein the amount of the cytolytic agent added to the solution of the platelet preparation is 0.2 to 5% (w/v).

4. The method for counting leukocytes according to claim 1, wherein the amount of the cytolytic agent added to the solution of the platelet preparation is 0.2 to 2% (w/v).

5. The method for counting leukocytes according to claim 4, wherein the cytolytic agent is selected from the group consisting of anionic surfactants, cationic surfactants, amphoteric surfactants and nonionic surfactants.

6. A method for counting leukocytes in a platelet preparation by staining the leukocytes, comprising:

placing a solution of the platelet preparation in an accumulation container comprising an opening, a sidewall portion, and a flat bottom portion having a membrane filter through which leukocytes are impassable, a part or all of the sidewall portion having a horizontal sectional area gradually increasing in a direction from the flat bottom portion towards the opening, filtering the solution of the platelet preparation through the membrane filter provided at the flat bottom portion of the accumulation container containing the solution of the platelet preparation to accumulate the leukocytes on the membrane filter, adding a surfactant and a dye to the leukocytes accumulated on the flat bottom portion to bare nuclei of the leukocytes and stain the leukocytes, and counting the stained leukocytes.

7. A method for counting leukocytes in an erythrocyte preparation by staining leukocytes, comprising:

mixing and shaking a solution of the erythrocyte preparation, a cytolytic agent capable of baring nuclei of leukocytes and solubilizing erythrocytes and a dye, in an accumulation container comprising an opening, a sidewall portion and a flat bottom portion, a part or all of the sidewall portion having a horizontal sectional area gradually increasing in a direction from the flat bottom portion towards the opening, to solubilize erythrocytes, bare nuclei of the leukocytes and stain the leukocytes, centrifuging the accumulation container to accumulate the stained leukocytes on the flat bottom portion of the accumulation container, and counting the stained leukocytes.

8. The method for counting leukocytes according to claim 7, wherein the cytolytic agent is selected form the group consisting of anionic surfactants, cationic surfactants, amphoteric surfactants and nonionic surfactants.

9. The method for counting leukocytes according to claim 7, wherein the amount of the cytolytic agent added to the solution of the erythrocyte preparation is 0.1 to 10% (w/v).

10. The method for counting leukocytes according to claim 7, wherein the amount of the cytolytic agent added to the solution of the erythrocyte preparation is 0.1 to 3% (w/v).

11. The method for counting leukocytes according to claim 10, wherein the cytolytic agent is selected form the group consisting of anionic surfactants, cationic surfactants, amphoteric surfactants and nonionic surfactants.

12. An apparatus for counting leukocytes comprising:

a leukocyte accumulation container comprising an opening, a flat bottom portion and a sidewall portion, a part or all of the sidewall portion having a horizontal sectional area gradually increasing in a direction from the flat bottom portion towards the opening, a lens portion for projecting the state of the flat bottom portion of the leukocyte accumulation container as an image of which magnification can be changed by the lens portion, detection means for detecting the number of the leukocytes accumulated on the flat bottom portion of the leukocyte accumulation container by analyzing the image of the flat bottom portion of the leukocyte accumulation container projected via the lens portion, and output means for outputting detection results obtained by the detection means, wherein the detection means comprises an image-capturing portion having an image-capturing surface for capturing an image of the flat bottom portion of the leukocyte accumulation container projected via the lens portion, an image analysis processor that identifies leukocytes in the image of the flat bottom portion of the leukocyte accumulation container on the image-capturing surface and a counter for leukocyte count, and the flat bottom portion of the leukocyte accumulation container has a size such that the image of the entire flat bottom portion is in the image-capturing surface of the detection means as one image.

13. The apparatus for counting leukocytes according to claim 12, wherein the image-capturing portion comprises CCD image-processing means.

14. The apparatus for counting leukocytes according to claim 12, wherein said flat bottom portion has a membrane filter through which leukocytes are impassable.

15. The apparatus for counting leukocytes according to claim 12 or 14, wherein the flat bottom portion has a maximum diameter of 0.2 to 5 mm.

* * * * *